(12) United States Patent
Panian

(10) Patent No.: US 10,058,684 B1
(45) Date of Patent: Aug. 28, 2018

(54) METHOD AND DEVICES FOR PASSING A CHRONIC TOTAL OCCLUSION AND RE-ENTRY INTO A TRUE LUMEN

(71) Applicant: Justin Panian, San Francisco, CA (US)

(72) Inventor: Justin Panian, San Francisco, CA (US)

( * ) Notice: Subject to any disclaimer, the term of this patent is extended or adjusted under 35 U.S.C. 154(b) by 0 days.

(21) Appl. No.: 15/832,600

(22) Filed: Dec. 5, 2017

(51) Int. Cl.
| | | |
|---|---|---|
| *A61M 29/00* | (2006.01) |
| *A61M 25/10* | (2013.01) |
| *A61B 17/3203* | (2006.01) |
| *A61M 25/01* | (2006.01) |
| *A61B 17/22* | (2006.01) |

(52) U.S. Cl.
CPC ..... *A61M 25/104* (2013.01); *A61B 17/32037* (2013.01); *A61M 25/0194* (2013.01); *A61B 2017/22001* (2013.01); *A61B 2017/22044* (2013.01); *A61B 2017/22095* (2013.01); *A61M 2025/018* (2013.01)

(58) Field of Classification Search
CPC ............ A61M 25/104; A61M 25/0194; A61M 2025/018; A61B 17/32037; A61B 2017/22001; A61B 2017/22044; A61B 2017/22095
See application file for complete search history.

(56) References Cited

U.S. PATENT DOCUMENTS

| | | | |
|---|---|---|---|
| 8,206,370 B2 | 6/2012 | von Oepen et al. |
| 9,788,855 B2 | 10/2017 | Kugler et al. |
| 2001/0029396 A1* | 10/2001 | Wilson | A61F 2/856 623/1.11 |
| 2009/0198178 A1* | 8/2009 | Gurm | A61F 2/954 604/96.01 |
| 2017/0259033 A1* | 9/2017 | Erickson | A61M 25/0026 |
| 2017/0296794 A1 | 10/2017 | Kugler et al. |

FOREIGN PATENT DOCUMENTS

WO    WO 03097122 A2 *  11/2003   ............. A61B 17/22

OTHER PUBLICATIONS

F Hussain, MD et al.,—"A Complex Dissected Chronic Occlusion: Targeted Balloon Dilatation of False Lumen to Access True Lumen Combined Localized Subintimal Tracking and Re-Entry, Parallel Wire, Contralateral Injection, and Useful Antegrade Lumen Re-entry Technique" Catheter Cardiovasc. Interv. 2017; 1-4.
D. Dash MD,—"Guidewire Crossing Techniques in Coronary Chronic Total Occlusion" Indian Heart Journal 68 (2016) 410-420.
P.Schneider, MD et al—"Re-Entry into the True Lumen from Subintimal Space" J Vasc Surg 2013; 58:529-34.

* cited by examiner

*Primary Examiner* — Ashley Fishback

(74) *Attorney, Agent, or Firm* — Raymond Sun

(57) ABSTRACT

Methods and devices are disclosed for passing Chronic Total Occlusion (CTO) from subintimal location and re-entry into a true-lumen of the patient using transient fenestration approach. The transient fenestration is induced by balloon dilatation within the CTO, and a guidewire quickly trails into a true lumen.

4 Claims, 5 Drawing Sheets

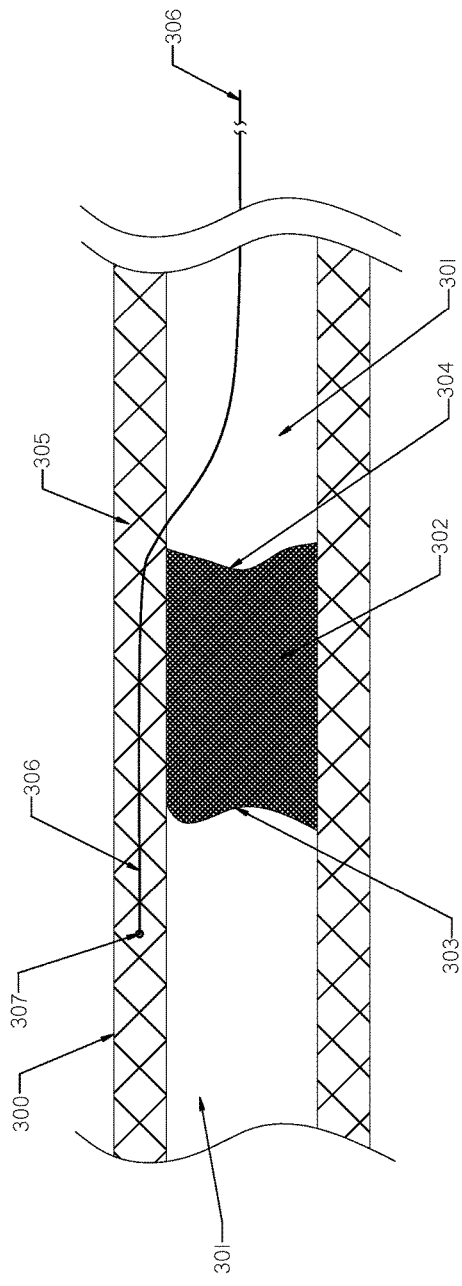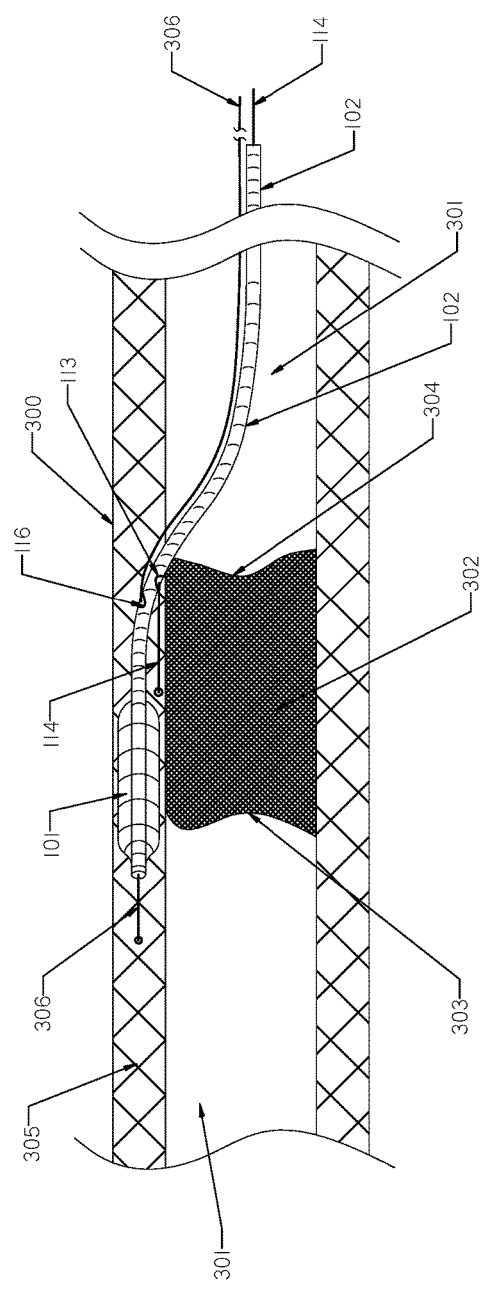
Fig. 3
Fig. 4

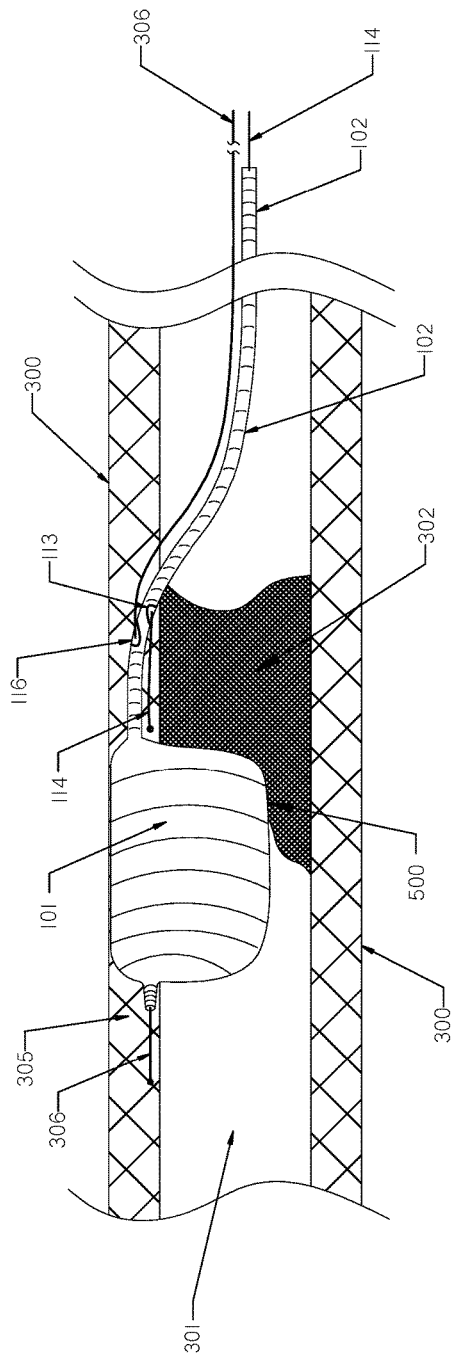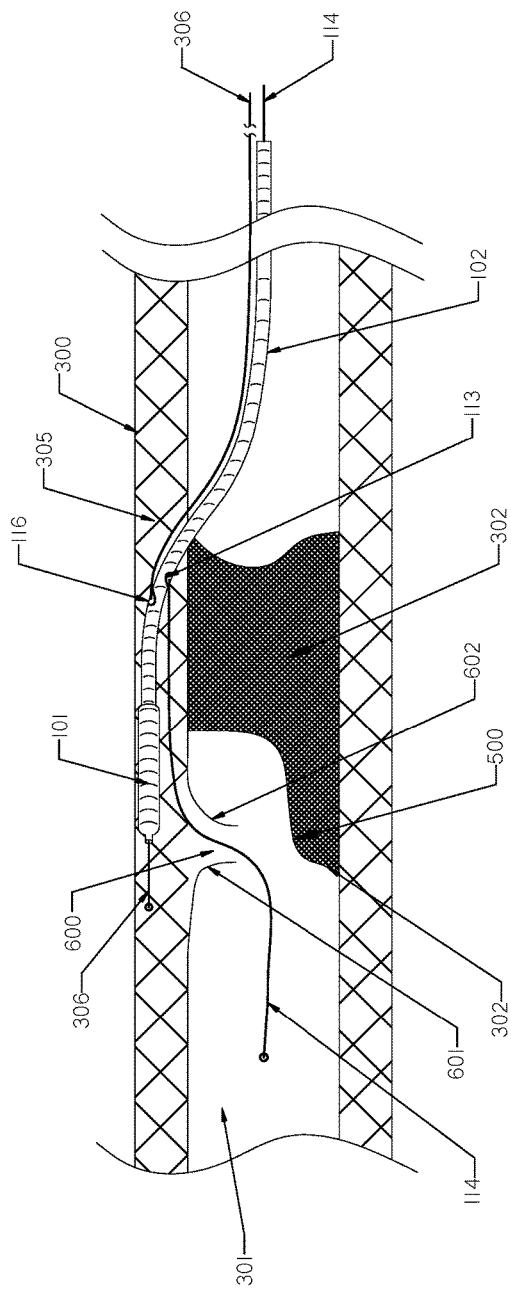
Fig. 5
Fig. 6

METHOD AND DEVICES FOR PASSING A CHRONIC TOTAL OCCLUSION AND RE-ENTRY INTO A TRUE LUMEN

BACKGROUND OF THE INVENTION

1. Field of the Invention

The present invention describes devices and methods for passing or crossing Chronic Total Occlusions (CTO). More particularly, the invention describes devices and methods for guidewire re-entry from the subintimal space to the distal true lumen while treating chronic occlusion, and establishing a vehicle for other interventions to follow, and to re-establish blood flow past the CTO.

2. Description of the Related Art

Age, high cholesterol and other factors are causing arterial atherosclerosis and vascular disease, and can cause vascular occlusions that are frequently called CTO. CTO's are well-organized tissue that is often calcific, and which completely block blood flow, thereby completely occluding portions of the patient's vasculature and presenting significant risks to a patient's health. A coronary artery CTO may result in painful angina, loss of cardiac tissue or patient death. A CTO of the femoral and/or popliteal arteries in the leg may result in limb-threatening ischemia and potential limb amputation.

Angioplasty is the most common treatment for CTO, and crossing a CTO is one of the most challenging procedures for interventional clinicians. Recanalizing CTOs can improve exercise capacity, symptoms and possibly reduce mortality. Many strategies such as escalating wire stiffness, parallel wire, see-saw, contralateral injection, subintimal tracking and re-entry (STAR), retrograde wire techniques (controlled antegrade retrograde subintimal tracking—CART), reverse CART, confluent balloon, rendezvous in coronary, and looping wire, among others, have been described in the prior art.

Current endovascular devices and techniques frequently fail to cross CTO, often landing a CTO crossing guidewire in a subintimal space with endless efforts to re-cross the CTO into a true lumen. Much time is spent to re-enter into a true lumen with a high risk of perforating a vessel. Consequently, the challenge of crossing a CTO is still incomplete and there is a need for further technical improvements.

SUMMARY OF THE INVENTION

Methods and devices disclosed herein are suitable as the first-line approach/therapy to cross a CTO by placing a guidewire intentionally in a subintimal space, or for a bailout approach of a failed true-to-true lumen CTO crossing when the guidewire ends in a subintimal space after multiple failed attempts to cross the CTO true-to-true lumen.

The present invention describes devices and methods employed to cross a CTO by entering the wall of a vascular lumen for bypassing the CTO. Entry into a vascular wall involves the passage of an endovascular device into and out of the wall which is often described as false lumen access, intramural access, submedial access or otherwise commonly called subintimal space access.

A novel CTO passing and re-entry method, and associated devices, are proposed. For coronary CTO passing and re-entry, this can be called antegrade transient fenestration and guidewire re-entry. For passing a CTO in peripheral arteries, this can be called antegrade, retrograde, contralateral or brachial transient fenestration and guidewire re-entry, depending on the specific access approach.

Methods of the present invention include creating fenestrations, or the opening of the dissection, or creating flaps between the false and true lumens. This is achieved by advancing a slightly undersized balloon into the subintimal space, and inflating it across the distal cap of the CTO and creating fenestration. After balloon deflation, a soft (slippery) polymer-jacketed guidewire is then advanced across the fenestration created by balloon inflation from the subintimal space into the true lumen.

Methods of the present invention can be performed within 30 seconds from the moment when the balloon catheter is deflated in a subintimal space because the fenestration tends to quickly close. The sooner a guidewire slides through the fenestration, the easier it is to place it in the true lumen, preferably within 10 seconds. The fenestration is usually opened the widest in the first few seconds, and tends to close quickly within the next few seconds.

Embodiments of the present invention also include a low-profile balloon catheter that is suitable for entering the subintimal space, and then dissecting or opening a fenestration between a subintimal space and a true lumen, and which can be easily removed. Preferably, such balloon catheters should be equipped with three lumens, one lumen for the balloon inflation and deflation and two guidewire lumens, one guidewire lumen for placement of the balloon catheter at the fenestration area, and one guidewire lumen for re-entry in a true lumen.

In another embodiment of the present invention, the balloon catheter has at least two guidewire lumens. Each guidewire lumen is preferably a separate guidewire lumen; however, the lengths, distal exits/entry and proximal exits/entry may have different locations.

Different locations for the proximal entry of the guidewire lumens also provide a differentiation for the operator where guidewires in these lumens are designated.

The balloon catheter of the present invention provides the benefits of both an over-the-wire balloon catheter and a rapid-exchange balloon catheter. Such unique features allow the balloon catheter to be placed at the treatment location using one guidewire, while another guidewire may be used for clinical procedures

BRIEF DESCRIPTION OF THE DRAWINGS

FIG. 3 is enlarged view of a CTO with a guidewire in a subintimal space.

FIG. 4 shows the balloon catheter of FIG. 1A in the subintimal space of FIG. 3.

FIG. 5 shows the balloon catheter of FIG. 4 inflated in the subintimal space of FIG. 3.

FIG. 6 shows the balloon of FIG. 5 deflated and a second guidewire advanced from the guidewire lumen through fenestration and into a distal true lumen.

DESCRIPTION OF THE PREFERRED EMBODIMENTS

Figure 1:
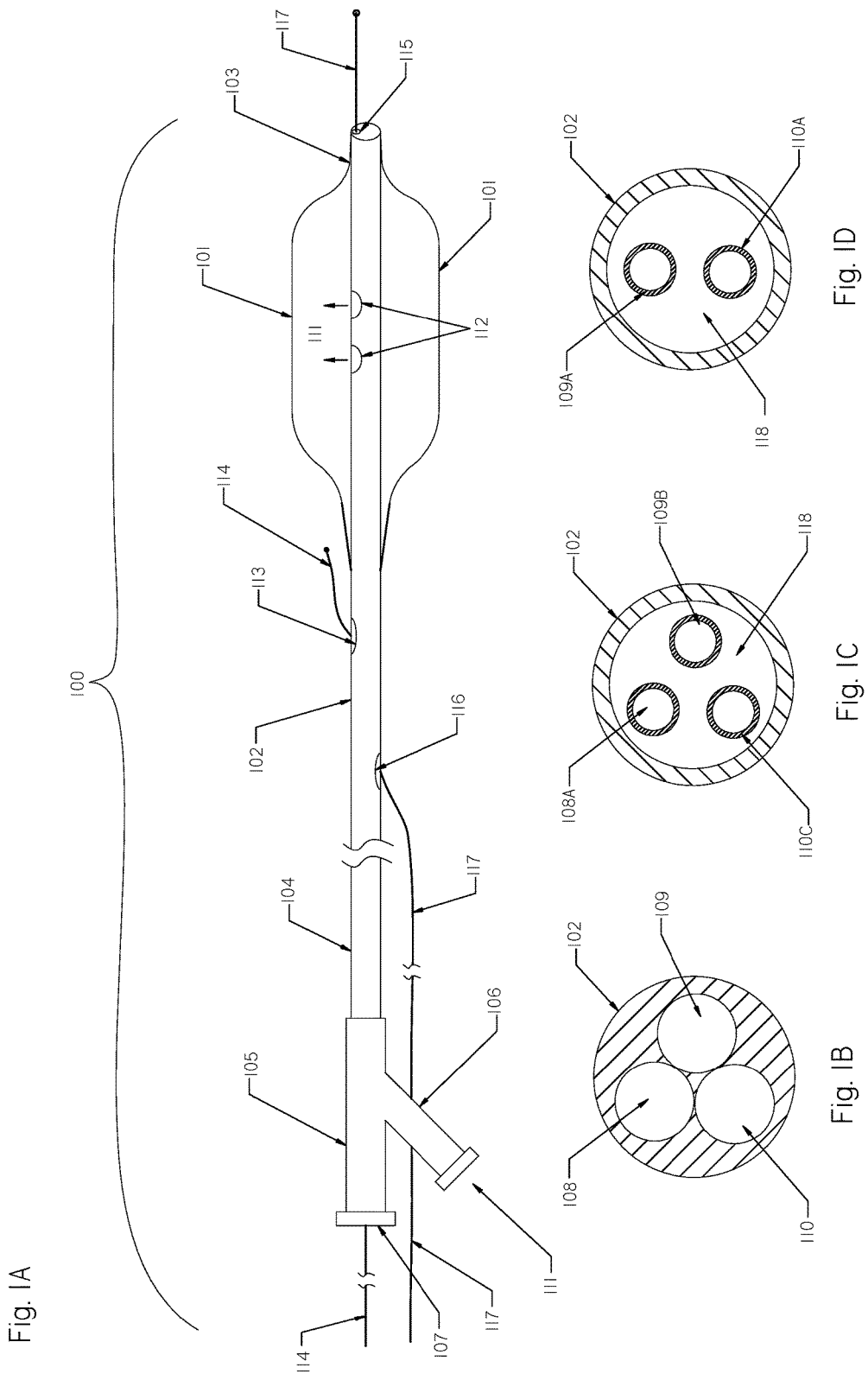
FIG. 1A is a plan view of a balloon catheter with dual guidewire lumens according to the present invention.
FIG. 1B is a cross-sectional view of the catheter in FIG. 1A showing three lumens.
FIG. 1C is a cross-sectional view of the catheter in FIG. 1A showing three lumens according to an alternative embodiment.
FIG. 1D is a cross-sectional view of alternative embodiment of the catheter of FIG. 1A.

As used herein, "subintimal space" and "re-entry from subintimal space" are related to passing or crossing a chronic total occlusion, and pertains to the area beneath the intima and adventitial layers in a blood vessel.

The terms "balloon" and "balloon catheter" refer to the catheter having a balloon.

The terms "false lumen" and "subintimal space" refer to the same area and relates to the same tract.

The term "rapid exchange fashion" refers to a balloon catheter having a "second" guidewire lumen or rail with the entry at the distal end of the catheter and the exit at any location proximal to the balloon.

The term "over-the-wire fashion" refers to a balloon catheter having a "first" guidewire lumen or rail with the entry at the proximal end of the catheter and an exit at the distal portion of the catheter either distally to the balloon, proximally to the balloon or at the distal end of the balloon catheter.

FIG. 1A shows a balloon catheter 100 having a balloon 101 and a catheter shaft 102. The catheter shaft 102 has a distal end 103 and a proximal end 104. The catheter shaft 102 is connected at its proximal end 104 to a Y-connector 105, which has balloon inflation port 106 and a guidewire port 107. The catheter shaft 102 has three inner lumens as shown in FIG. 1B: a balloon inflation lumen 108, a first guidewire lumen 109 for placement of an over-the-wire guidewire, and a second guidewire lumen 110 for placement of a rapid-exchange guidewire.

The balloon 101 is inflated by infusing saline 111 (or saline in mixture with contrast) via an inflation port 106 and into the inflation lumen 108. The saline 111 is delivered into the balloon 101 through inflation holes 112.

To assure delivery and infusion of saline 111 inside the balloon 101, continuity of the inflation lumen 108 is terminated internally before the distal end 103 of the catheter shaft 102. Terminating the continuity of the inflation lumen 108 may by accomplished by extruding a discontinuity, plugs, glue and other means (not shown).

The first guidewire lumen 109 is constructed for over-the-wire use. The entry into the first guidewire lumen 109 is located at the port 107 and the exit 113 is located proximally to the balloon 101. The guidewire 114 is introduced through the first guidewire lumen 109.

Alternatively, the exit 113 for the first guidewire lumen 109 may be situated at any proximal area from the location of the balloon 101 on the shaft 102, including the space within the balloon 101 (not shown). The exit 113 may also be located distally from the balloon 101, as well as at the exit from the distal end 103 of the catheter shaft 102 (not shown).

The second guidewire lumen 110 is constructed for rapid-exchange use. The entry 115 into the second guidewire lumen 110 is coaxially located on the distal end 103 of the catheter shaft 102. The exit for the guidewire from the second guidewire lumen 110 is located at the area 116. The exit area 116 may be situated at any location along the catheter shaft 102 proximal from the balloon 101 but before reaching the Y-connector 105. The guidewire 117 is introduced through the second guidewire lumen 110.

The guidewire lumens 109 and 110 may be made within one continuous extrusion and included together with the balloon inflation lumen 108 in the catheter shaft 102 as shown in FIG. 1B. Alternatively, separate individual tubes 108A, 109B 110C may be extended coaxially inside the inner lumen 118 of the catheter shaft 102 as shown in FIG. 1C. The tube 108A may provide access for balloon inflation and deflation, while the tubes 109B and 110C may be provided for guidewire functions. Also, as shown in FIG. 1D, the inner lumen 118 of the shaft 102 may be used for delivering inflation medium for balloon inflation and deflation, while the separate tubes 109A and 110A may be provided for guidewire function.

Several alternative constructions for guidewire lumens are provided regarding locations for the first (over-the-wire) lumen 109 and the second (rapid-exchange) lumen 110. All these options are well-known in the art and will only be described herein without reference to any drawings.

The first guidewire lumen 109 for over-the-wire use may have the guidewire entry port located at the entry 107 as shown in FIG. 1A or anywhere at the proximal end 104 of the catheter shaft 102. The exit port 113 of the first guidewire lumen 109 may be located proximal to the balloon 101 as shown in the FIG. 1A. Also, the exit port 113 of the first guidewire lumen 109 may be located distal to the balloon 101 along the distal end 103 of the balloon catheter shaft 102 (not shown). Alternatively, the exit port 113 of the first guidewire lumen 109 may be located at the very distal end 115 of the catheter shaft 102 (not shown).

The second guidewire lumen 110 for rapid-exchange use may have the guidewire entry port at the distal end 103 of catheter shaft 102, with the exit port located proximal to the balloon 101 or distally to the balloon 101.

Furthermore, the dual lumen balloon catheter may have two guidewire lumens, both constructed for over-the-wire use. In such a case, the first and the second guidewire lumens will have guidewire entry ports at the proximal end of the catheter shaft and the exit ports at the distal end of the catheter shaft (not shown).

The dual lumen balloon catheter may also have two guidewire lumens, both constructed for rapid exchange use. In such a case, the first and the second guidewire lumens will have guidewire entry ports at the distal end of the catheter shaft and the exit ports proximal to the balloon (not shown).

FIG. 1 shows the balloon catheter 100 with dual guidewires having three lumens, a balloon inflation and deflation lumen 108, a first guidewire lumen 109, and a second guidewire lumen 110. The internal structure of the shaft 102 may include one extrusion with three lumens as shown in FIG. 1B, or have separate tubes 108A, 109B and 110C coaxially extending inside the lumen 118 of the shaft 102 as shown in FIG. 1C, or have two separate lumens 109A and 110A inside the inner lumen 118 of the shaft 102, as shown in FIG. 1D.

The balloon 101 preferably comprises a non-compliant balloon made of relatively non-elastic material, including but not limited to, medium density polyethylene, linear low-density polyethylene, polyethylene terephthalate, nylon, polyester, or any of a variety of other medical grade polymers known for this use in the medical balloon art. Preferably, the geometry and balloon materials will withstand an internal pressure of at least 8 atmospheres without any leakage or rupture. The fluid to inflate the balloon 101 may be saline, contrast or saline diluted contrast that is introduced at any suitable rate as preferred by the physician.

The balloon 101 may be made with reinforcement, implemented cutting edges or other features to improve its ability to create fenestration in the subintimal space. Balloons with such features are well known in the art, including but not limited to: AngioSculpt™ Balloon (Spectranetics Colorado Springs, Colo.), Chocolate™ Balloon (TriReme Fremont, Calif.), and VascuTrack™ (Cardinal Health Dublin, Ohio).

Materials used for the catheter and the guidewires are well-known in the art and no additional description will be provided.

FIG. 2A shows an alternative balloon catheter 200 according to the present invention comprising a balloon 201 and a shaft 202 having the distal end 203 and proximal end 204. The proximal end of the shaft 204 is attached to a Y-connector 205 having an inflation port 206 and a guidewire port 207. An irrigation lumen 208 and a guidewire lumen extend longitudinally along the shaft 202. The balloon 201 is inflated with saline 210 via an inflation port 206 and outlet ports 211 located inside the balloon 201. The guidewire lumen is divided into two lumen segments, a first over-the-wire lumen segment 209A and a second rapid-exchange lumen segment 209B.

The second rapid exchange lumen segment 209B extends through the distal portion 212, and has an entry port 213 located on the distal end 203 of the shaft 202, and an exit port 214 located on the shaft 202 proximal to the balloon 201. A rapid-exchange guidewire 215 is shown extending through the second rapid exchange lumen segment 209B in the distal portion 212.

The first over-the-wire lumen segment 209A extends through the proximal portion 216, and has an entry port 207 and an exit port 217 that are both located proximal to the port 214. An over-the-wire guidewire 218 is shown extending through the the first over-the-wire lumen segment 209A in the proximal portion 216.

The balloon 201 is inflated by infusing saline 210 (or saline in mixture with contrast) via the inflation port 206 and into the inflation lumen 208. The saline 210 is delivered into the balloon 201 through inflation holes 211.

FIG. 2B shows the cross-section A-A of the shaft 202 with the irrigation lumen 208 and the first over-the-wire lumen segment 209A along the length of the proximal portion 216. FIG. 2C shows the cross-section B-B of the shaft 202 between the exit ports 214 and 217, where there is no guidewire lumen and only the irrigation lumen 208. FIG. 2D shows the cross-section C-C of the shaft 202 with the irrigation lumen 208 and the second rapid exchange lumen segment 209B along the length of the distal portion 212.

Thus, the guidewire lumen does not extend within the shaft 202 at the area around the cross-section B-B. This area constitutes an interruption of the guidewire lumen in this area, and may be achieved by extruding a discontinuity, providing plugs, using glue, and other suitable means.

Several alternative constructions for guidewire lumens can be provided regarding locations for the exit and the entry of the first over-the-wire lumen segment 209A and the second rapid-exchange lumen segment 209B. All these options are known in the art and will only be described herein without reference to any drawings.

The first over-the-wire lumen segment 209A may have the guidewire entry port located at the entry 207 as shown in FIG. 2A or anywhere at the proximal end 204 of the catheter shaft 202, and the exit port may be located at the exit 217 or anywhere along the catheter shaft 202 proximal to the balloon 201.

The second rapid exchange lumen segment 209B may have the guidewire entry port at the distal end 213 of catheter shaft 102, and the exit port 214 located anywhere proximal to the balloon 201.

Alternatively, separate tubes may be used inside the shaft 202: one tube for inflating and deflating the balloon 201, one separate tube for the first over-the-wire lumen segment 209A attached on one end to the exit 217 and on the other end to the entry port 207, and one separate tube for the second rapid exchange G lumen segment 209B attached on one end at the distal end 103 of the shaft 102 and on the other end attached at the exit 214.

Figure 2:
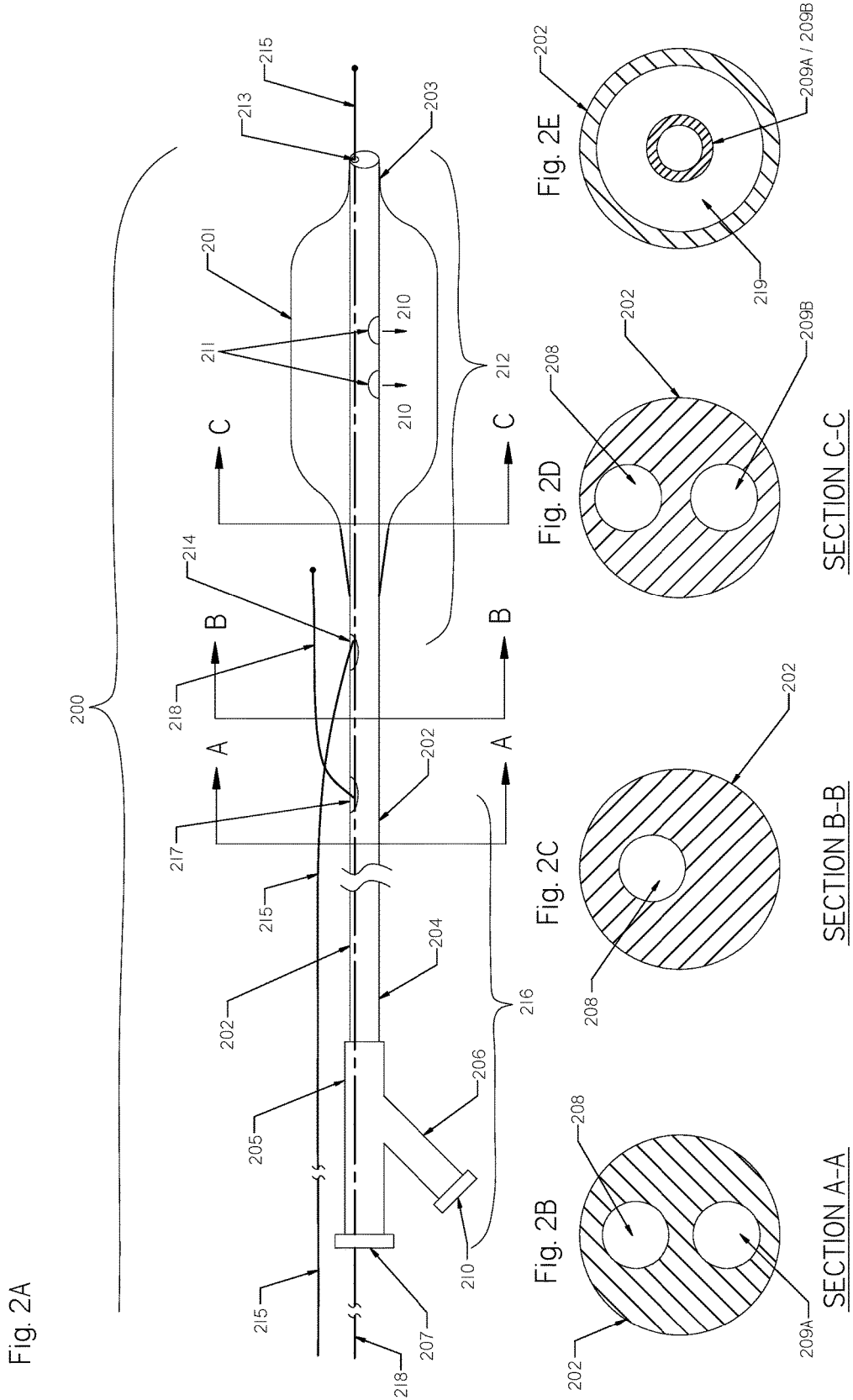
FIG. 2A is a plan view of an alternative balloon catheter according to the present invention having one guidewire lumen utilized for two guidewires.
FIG. 2B is a cross-sectional view of the catheter taken along line A-A in FIG. 2A.
FIG. 2C is a cross-sectional view of the catheter taken along line B-B in FIG. 2A.
FIG. 2D is a cross-sectional view of the catheter taken along line C-C in FIG. 2A.
FIG. 2E is a cross-sectional view of alternative embodiment of the catheter of FIG. 2A taken along either line A-A or C-C.

Thus, FIG. 2 shows the balloon catheter shaft 202 comprising two lumens 208 and 209A/209B extruded from the body of the catheter shaft 202. Alternatively, as shown in FIG. 2E, the catheter shaft 202 can be provided with an inner lumen 219, and a separate guidewire tube 209A/209B may be coaxially extended inside the inner lumen 219. In this embodiment, the inner lumen 219 functions to deliver inflation medium for balloon inflation and deflation.

FIGS. 1A and 2A show several different locations for the guidewire exit ports and entry ports. The entry and exit ports for these guidewire lumens are not limited to locations along the same axial line, as they can be radially offset from each other at any desired angle.

The guidewires 114 and 117 in FIG. 1 and the guidewires 215 and 218 in FIG. 2 are not limited to any guidewire dimension, length or structure, and can be any conventional guidewire.

FIG. 3 shows a blood vessel 300 having a true lumen 301, and a CTO 302 located inside the vessel 300 having a distal cap 303 and proximal cap 304. The CTO 302 is inadvertently wired in a subintimal fashion into the subintimal space 305 with the guidewire 306 having a distal end 307. The distal end 307 of the guidewire 306 is located beyond the distal cap 303 of the CTO 302 and in the subintimal space 305.

The guidewire 306 may be navigated at the beginning of the passing of the CTO 302 in the subintimal space 305 of the vessel 300. Such a scenario will be considered as an intentional subintimal crossing of CTO 302. However, most of interventional clinicians will attempt to cross the CTO 302 within the true lumen 101 and through the CTO 302. After a minute or so of probing the CTO 302 with the guidewire 306, the clinician will quickly understand the morphology of the CTO 302 and either decide to continue with a different kind of guidewire hoping to cross CTO 302 in the true lumen 301, or to place the guidewire 306 in the subintimal space 305.

Once the distal end 307 of the guidewire 306 is in the subintimal space 305, re-entry of the guidewire 306 into the vessel 300 should be attempted as close as possible to the distal cap 303 of the CTO 302, and far from the beginning of any side branches. This will minimize the risk of damaging any side branches during the guidewire manipulations, and maximize the likelihood of achieving a good distal flow.

The subintimal technique creates a neo-lumen between the intimal and adventitial layers of the arterial wall, displacing the atheromatous and calcified intimal and medial layers to the contralateral side of the vessel lumen (not shown) and producing a relatively smooth flow lumen.

Subintimal peripheral recanalization and angioplasty of the femoral and popliteal arteries are widely practiced and have diminished reliance upon bypass as first-line therapy. Re-entry into the true lumen is usually the most time-consuming part of interventional procedures. Improved CTO guidewires and support catheters, pedal access, re-entry catheters, and CTO crossing devices have recently been developed that significantly improve true lumen and subintimal crossings. However, as in coronary CTO crossing, re-entry in the femoral and popliteal arteries may be challenging, especially in the presence of calcification.

The subintimal space made by a guidewire is a strong factor of unsuccessful recanalization of CTOs. Once the subintimal space is created by a guidewire, the guidewire tends to slip into this space repeatedly and extend it along the circumference of the media of the vessel wall. If this happens, it is difficult to reach the distal true lumen or re-enter into the distal true lumen.

The most difficult part of a CTO passing or crossing procedure is to penetrate tissue at the distal end of the CTO to reach the distal true lumen 301. The major reason is the presence of enlarged false lumens in subintimal space made by a guidewire around the distal true lumen.

Re-entry into the true lumen 301 with the guidewire 306 should be performed as close as possible to the distal cap 303 of the CTO 302 and away from the takeoff of side branches so as to minimize the subintimal track and the risk of losing side branches.

FIG. 4 shows the dual guidewire balloon catheter 100 of FIG. 1 introduced over a guidewire 306 located in the second rapid-exchange guidewire lumen 110 into the subintimal space 305. The balloon 101 is located across of the distal cap 303 of the CTO 302. The second guidewire 114 is extended through the first over-the-wire guidewire lumen 109 slightly outside of the exit port 113.

The balloon 101 is sized 1:1 or less as compared to the vessel 300 diameter to avoid perforation of the vessel 300 when the balloon 101 is inflated. For example, if the vessel 300 size is 3 mm, the appropriate size of the balloon 101 should be 2.5 mm. Using a nominal balloon inflation pressure with non-compliant balloons would assure that the 1:1 ratio between the balloon size and vessel diameter will never be exceeded.

FIG. 5 shows the balloon 101 of the FIG. 1A inflated across the distal cap 303 of the CTO 302 such that inflating the balloon 301 will partially dilate the distal cap 303. The diameter of the inflated balloon 101 should be equal to or slightly smaller than the size of the vessel 300 to avoid perforations in the vessel 300.

Dilatation of the balloon 101 within the subintimal space 305 over the distal portion 303 of the CTO 302 will squeeze and dilate the area of the distal cap 303 as shown by arrow 500 towards the vessel 300. Thus, the balloon 101 creates tears, rips, splits, slashes, slits or snags of the dissected portion. Alternatively, the balloon device of FIG. 2A may be used instead of the balloon device 100 of FIG. 1.

FIG. 6 shows the balloon 101 of FIG. 5 deflated. After the balloon 101 is deflated, a fenestration 600 between the subintimal space 305 and the true lumen 301 is created with split flaps 601 and 602. The second guidewire 114 is advanced from the first over-the-wire lumen exit 113 through the fenestration 600 into the distal true lumen 301. Once the guidewire 114 is positioned in the true lumen 301 of the vessel 300, a conventional angioplasty (e.g., including but not limited to conventional balloon angioplasty, stenting or the use of drug eluting balloons) will follow.

The fact that the balloon 101 is partially positioned on the distal cap 303 of the CTO 302 may be a contributing factor in creating the fenestration 600. Presence of a harder plaque within the balloon 101 inflation space may serve as a "cutting" element and further facilitate creation of the fenestration 600.

The re-entry guidewire 114 should preferably be a polymer-jacketed, low tip-load guidewire, which can be one of the following: Sion Black™ or Fielder™ family, Asahi Intecc, Nagoya, Japan; or Fighter™, Boston Scientific; for ease and smooth manipulation and advancement.

Often, in clinical reality, there is no clear defining line between where the distal cap 303 of the CTO 302 ends and where a healthy vessel begins. Frequently, the presence of plaque or calcification appears in the vessel 300 distal to the distal cap 303 of the CTO 302. In such a circumstance, harder plaque or calcification can help to create a fenestration when there is a need to dilate the balloon again and create another fenestration.

The orientation of the guidewire exit port 113 of the catheter shaft 102 within the subintimal space 305 should preferably be directed towards the true lumen 301 during inflation and deflation of the balloon 101. Use of a directional L-shape radiopaque marker at the exit port 113 location may be helpful to direct the guidewire 114 into the true lumen 301 (not shown).

Once the guidewire 114 is advanced into the true lumen 301, a conventional angioplasty can follow that may include, but is not limited to, deployment of a drug eluting stent or drug eluting balloon. More detailed illustrations showing fenestration between the subintimal space 305 and the true lumen 101 are shown in FIGS. 7A, 7B, 7C, 7D.

When the balloon 101 is deflated, the guidewire 114 must be manipulated quickly to smoothly pass through the fenestration 600 from the subintimal space 305 and into the true lumen 301. Multiple approaches may be required to pass the second guidewire 114 from the subintimal space 305 into the true lumen 301. If the clinician has trouble to re-enter the guidewire 114 into the true lumen 301, the process of dilating the balloon 101 to create another fenestration 600 may be repeated again at a more distal location.

Figure 7A:
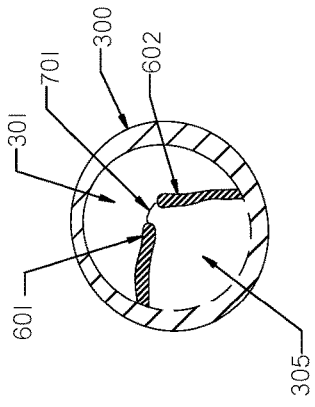
FIGS. 7A, 7B, 7C and 7D illustrate cross-sectional views of the fenestration between a false lumen and true lumen within 0-30 seconds after balloon deflation.

FIG. 7A illustrates a cross-sectional view based on a schematic Intravascular Optical Coherence Tomography (OCT) picture inside the vessel 300 and after the balloon 101 has been deflated and removed. The fenestration 600 between the false lumen or subintimal space 305 is opened to its widest extent. The dissection flaps 601 and 602 created during the balloon 101 inflation as shown in FIG. 5 expose a wide aperture from the subintimal space 305 into the true lumen 301. OCT analyses indicate that such wide fenestration will stay open approximately 3-4 seconds.

Figure 7B:
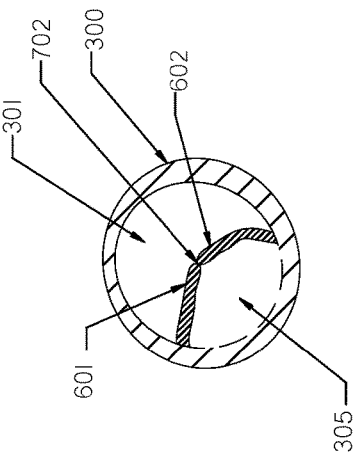

FIG. 7B illustrates the same area as in FIG. 7A at a timing of 4-5 seconds from the balloon 101 deflation. The fenestration 700 is becoming smaller than the fenestration 600 shown in FIG. 6A.

Figure 7C:
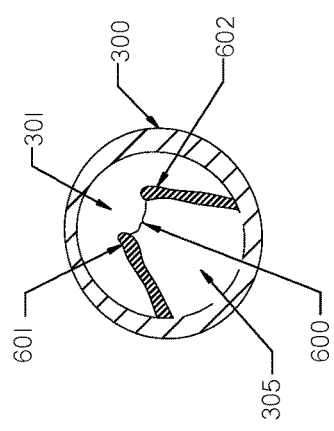

FIG. 7C illustrates the same area as in FIGS. 7A & 7B at a timing of 10 seconds after the balloon 101 deflation. The fenestration 701 is further narrowing and the dissection flaps 601 and 602 are getting close to each other. Thus, this indicates that the fenestrations 600, 700 and 701 between the subintimal space 305 and the true lumen 301 after the balloon 101 deflation are transient in the nature.

Figure 7D:
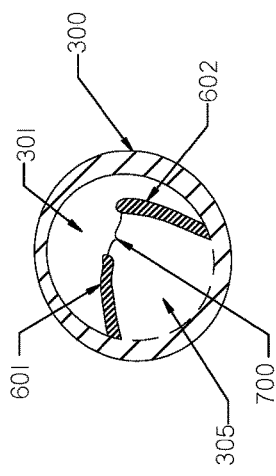

FIG. 7D illustrates the same area as in FIGS. 7A, 7B & 7C at a timing of 30 seconds after the balloon 101 deflation. The fenestration 702 has disappeared and the dissection flaps 601 and 602 are almost closed. This further validates the fact that the fenestration 600 between the subintimal space 305 and the true lumen 301 after the balloon 101 deflation will narrow after 10 seconds, and be almost closed after 30 seconds. The opportunity to sneak the re-entry guidewire 114 from the subintimal space 305 into the true lumen 301 will diminish after 30 seconds from balloon 101 deflation.

Frequently, multiple approaches are required to slide the re-entry guidewire 114 through the fenestration 600 to pass the re-entry guidewire 114 into the true lumen 301. If the passing of the re-entry guidewire 114 is not successful within the 30 seconds from the time when the first fenestration was created, it would be desirable to dilate the balloon 101 again and create another fenestration, preferably at slightly more distal location.

Crossing of the CTO and re-entry approaches described in the present invention carry the risk of arterial perforations. While perforations in peripheral arteries are less dangerous, perforations in coronary arteries may cause cardiac tamponade that constitutes the most severe clinical consequence. In the case of perforations, the balloon devices of the present invention may provide at least a temporary vehicle to stop bleeding and provide time for the clinician to proceed with other procedural steps, if needed, including cover stent placement or micro-coils deployment if the perforation is located in the distal portion of the vessel and it is not possible to heal with prolonged temporary balloon closure.

Some clinical, theoretical and hypothetical considerations have been introduced herein for explanation of how devices and methods of the present invention work and are effective; these considerations have been presented for providing a better understanding of the invention only, and do not limit the scope of the claims.

The above described embodiments of the invention are merely descriptive of its principles and are not to be considered limiting. Further modifications of the disclosed invention will occur to those skilled in the respective arts and all such modifications are deemed to be within the scope of the invention as defined by the following claims.

What is claimed is:

1. A dual guidewire lumen balloon catheter system, comprising:
   a first guidewire and a second guidewire; and
   an elongated catheter shaft having a distal portion with a distal end, a proximal portion with a proximal end, a balloon positioned adjacent the distal end of the elongated catheter shaft, an inflation lumen extending through the elongated catheter shaft and is fluidly coupled to the balloon, a first guidewire lumen segment that extends through the proximal portion of the catheter shaft, and a second guidewire lumen segment that extends through the distal portion of the catheter shaft, wherein the first guidewire extends through the first guidewire lumen segment, and the second guidewire extends through the second guidewire lumen segment;
   wherein the catheter shaft has an intermediate portion between the distal and proximal portions, wherein the intermediate portion only has a single lumen.

2. The system of claim 1, wherein the first guidewire lumen segment has an entry port at the proximal portion of the catheter shaft, and an exit port located along the catheter shaft proximal to the balloon.

3. The system of claim 1, wherein the second guidewire lumen segment has a guidewire entry port at the distal end of the catheter shaft, and an exit port located proximal to the balloon.

4. The system of claim 1 wherein the first and second guidewire lumen segments comprise two separate tubes.

* * * * *